US00PP10390P

United States Patent [19]

Hesse

[11] Patent Number: Plant 10,390

[45] Date of Patent: May 12, 1998

[54] CHRYSANTHEMUM PLANT NAMED 'RASPBERRY ICE'

[75] Inventor: Peter S. Hesse, Nipomo, Calif.

[73] Assignee: Clearwater Nursery, Inc., Nipoma, Calif.

[21] Appl. No.: 713,167

[22] Filed: Sep. 12, 1996

[51] Int. Cl.[6] ..... A01H 5/00

[52] U.S. Cl. ..... Plt./74.1

[58] Field of Search ..... Plt./74.1, 82.5

*Primary Examiner*—Howard J. Locker

*Attorney, Agent, or Firm*—Arnold, White & Durkee

[57] ABSTRACT

The present invention comprises a new and distinct cultivar of Chrysanthemum, botanically known as *Dendranthema grandiflora*, and referred to by the cultivar name Raspberry Ice.

1 Drawing Sheet

BACKGROUND OF THE NEW PLANT

The female parent of Raspberry Ice was the commercial variety Ultralight (U.S. Plant Pat. No. 6,084), and the male parent was Marsala, an unpatented European variety. The cross was made in the summer of 1988.

Raspberry Ice was discovered and selected as a unique flowering plant within the progeny of the stated cross by Peter S. Hesse in October 1989 in a controlled environment at Clearwater Nursery in Nipomo, Calif. 93444, U.S.A. Compared to its female parent, Ultralight, Raspberry Ice has an 8.5 week response time compared to 9 weeks for the parent. Ultralight is lavendar in color compared to Raspberry Ice and has a tall, upright habit compared with the more spreading habit of Raspberry Ice. The new cultivar also differs from its male parent Marsala which has a clubby apprearance with flowers tightly arranged with gaps on individual branches. The upper ray floret color of Marsala is dark maroon while that of Raspberry Ice is greyed-purple.

Horticultural examination of controlled flowerings of successive plantings has shown that the unique combination of characterisitics as herein disclosed for Raspberry Ice are firmly fixed and are retained through successive generations of asexual reproduction. Asexual reproduction was accomplished when vegetative cuttings were taken in January, 1990 in a controlled environment in Nipomo, Calif.

Raspberry Ice has not been observed under all possible environmental conditions. The phenotype may vary significantly with variations in the environment such as temperature, light intensity and day length.

The following observations, measurements and comparisons describe plants grown in a controlled environment in Nipomo, Calif. Unrooted cuttings were directly stuck into 6.5" pots and grown under the natural temperature and day length prevailing in January through March of 1996.

The following traits have been repeatedly observed and are determined to be basic characteristics of Raspberry Ice, which in combination distinguish this Chrysanthemum as a new and distinct cultivar.

1. Flat capitulum form.
2. Daisy capitulum type.
3. Greyed-Purple fully expanded outer ray florets.
4. Yellow Daisy disc with green eye.
5. Diameter across the face of the capitulum of 10.2 cm.
6. Exceptional upright to spreading habit with an average of 4.6 breaks after a single pinch.

7. Flowering response is approximately 58 days from the start of short days.
8. Relatively easy to control plant height from bench such that the finished height will range from 16 inches to 18 inches depending on pot size and market requirements.

DESCRIPTION OF THE PHOTOGRAPHS

The accompanying photographic drawing shows a typical inflorescence and leaf characteristics of Raspberry Ice, with the colors being as nearly true as possible with illustrations of this type.

Sheet 1 is a color photograph of Raspberry Ice grown as a pinched spray mum with 5 cuttings in a 6.5" pot.

Of the commercial cultivars known to the inventor, the most similar in form, color, and habit to Raspberry Ice is the unpatented cultivar Maroon Akron. Chart A compares certain characteristics of Raspberry Ice to the same characteristics of Maroon Akron. Color designations are in reference to 1986 edition of R.H.S. Colour Chart first published in 1986 by the British Royal Horticultural Society, London, England. The plants were grown side by side in a controlled greenhouse environment. The growth regulator B-Nine™ was applied at a rate of 2,500 ppm in three applications. Comparisons were made in Nipomo, Calif.

CHART A

| | MAROON AKRON | RASBERRY ICE |
|---|---|---|
| CAPITULUM FORM | FLAT | FLAT |
| CAPITULUM TYPE | DAISY | DAISY |
| DIAMETER ACROSS FACE OF CAPITULUM | 6.7 CM | 10.2 CM |
| BRANCHING | UPRIGHT | UPRIGHT |
| PATTERN | SPREADING | SPREADING |
| BREAKS/PINCH | 6 | 4.6 |
| HEIGHT IN A 6.5" POT | 16–18 INCHES | 16–18 INCHES |
| DISC FLORET COLOR | MOSTLY YELLOW GREEN 151A | MOSTLY YELLOW GREEN 151A |
| # DISC FLORETS | 180 | 151 |
| LENGTH OF DISC FLORETS | 0.6 CM | 0.72 CM |
| RAY FLORET COLOR (FRONT) | 60A | 187C |
| # RAY FLORETS | 21.2 | 26 |
| SHAPE OF RAY FLORETS | ELLIPTIC | ELLIPTIC |
| LENGTH OF RAY FLORETS | 3.1 CM | 4.79 CM |
| WIDTH OF RAY FLORETS | .75 CM | 1.3 CM |

-continued

CHART A

| | MAROON AKRON | RASBERRY ICE |
|---|---|---|
| NUMBER OF FLOWERS/BREAK | 10.2 | 6.8 |
| LEAF COLOR | 137A UPPER<br>137C LOWER | 147A UPPER<br>147B LOWER |
| MATURE LEAF LENGTH | 11.4 CM | 10.3 CM |
| MATURE LEAF WIDTH | 5.4 CM | 5.1 CM |
| RESPONCE: TREATMENT | 8.5 WEEKS: Medium vigorous grower | 8.5 WEEKS: Medium vigorous grower |

The two cultivars are similar in having a flat, daisy capitulum, an upright, spreading branching pattern, a similar finished plant height, elliptic ray florets, a response time of 8.5 weeks from the start of short days, and each has a mostly yellow disc floret color. However, the diameter of the capitulum of Raspberry Ice is larger than the capitulum of Maroon Akron, Maroon Akron has more breaks per pinch than Raspberry Ice and Maroon Akron tends to have more disc florets than Raspberry Ice. Additionally, the length of the disc florets is greater for Raspberry Ice. Using The Royal Horticultural Society Colour Chart as a standard reference, the front ray floret color for raspberry Ice is greyed-purple 187C while the color of the front ray florets of Maroon Akron is red-purple 60A. Maroon Akron has fewer ray florets than Raspberry Ice and its ray florets that are longer in length. The width of the ray florets of Raspberry Ice is greater than Maroon Akron. The color of the leaves of Maroon Akron is slightly lighter green than the color of the leaves of Raspberry ice and it has longer mature leaves.

The Plant

Classification:

*Botanical.*—*Dendranthema grandiflora* CV. name Raspberry Ice.

*Commercial.*—Flat daisy to be grown primarily as a Spray/CBR (center bud removed) pot mum.

Inflorescence:

*Capitulum.*—Form: Flat. Type: daisy. Diameter across face: average of 10.2 cm.

*Corolla of ray florets.*—Color (general tonality from a distance of three meters): Yellow. Color: Front Fully Expanded Ray Floret: 187C. back Fully Expanded Ray Floret: 185D. Disc Floret Color. Edge begins with 14A to Center Green of 151A. Disc Diameter: 1.2 cm .

General appearance:

*Height.*—When grown in a 6.5" pot with 1-4 applications of B-Nine™ at a rate of 2500 ppm, the total plant height from the bottom of the pot may be maintained at 16 to 18 inches.

*Branching pattern.*—Upright and spreading with an average of 4.6 breaks when grown with one pinch.

*Foliage.*—Color (upper surface): 147A. Color (lower surface): 147B. Shape: See Photograph coarsely divided.

*Reproductive organs.*—Androecium: Present in disk florets. Gynoecium: Present in both ray florets and disk florets. Pollen: Scant.

What is claimed is:

1. A new and distinct chrysanthemum plant named 'Raspberry Ice' substantially as herein described and shown, characterized by the grey-purple color of the ray florets.

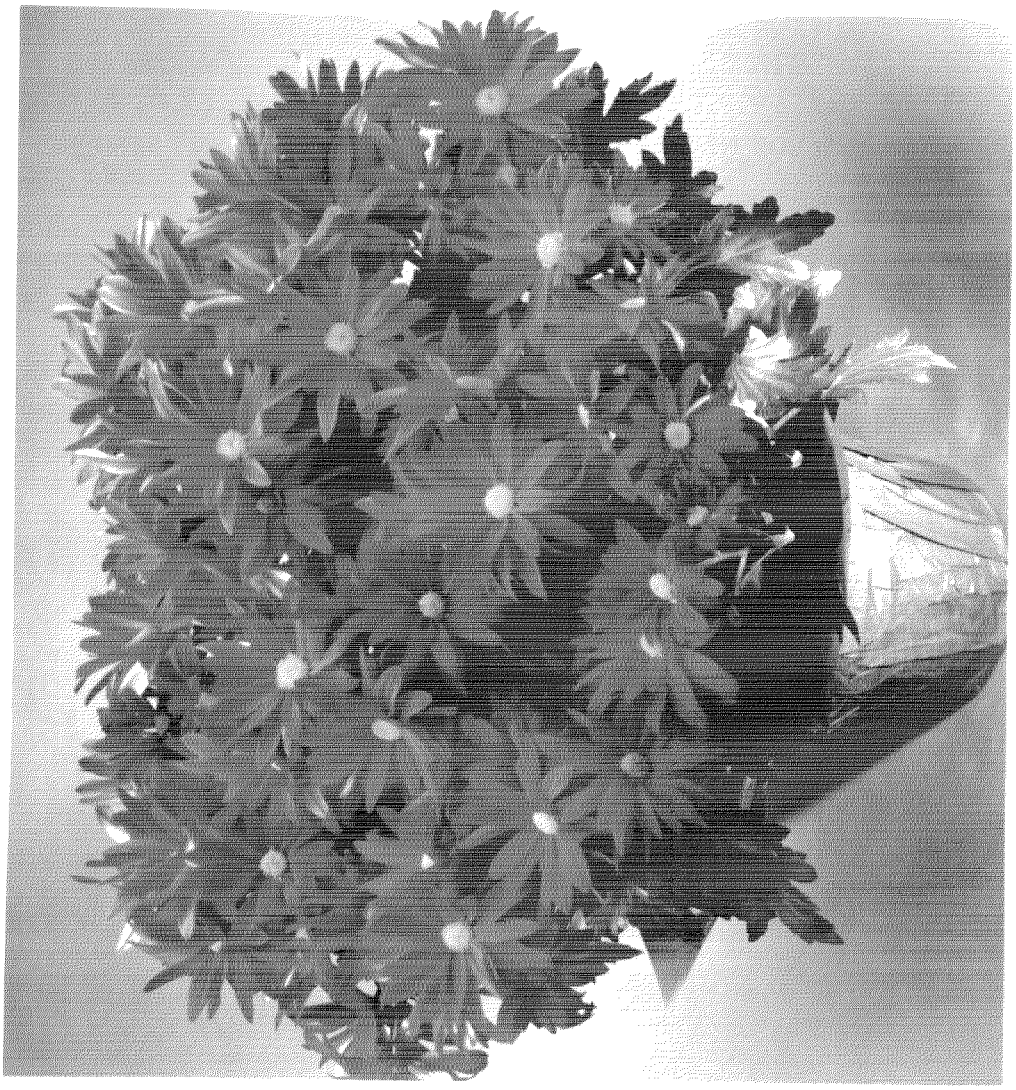

* * * * *